US00PP18147P3

(12) United States Plant Patent
Goffreda et al.

(10) Patent No.: US PP18,147 P3
(45) Date of Patent: Oct. 30, 2007

(54) NECTARINE TREE NAMED 'NJN100'

(50) Latin Name: *Prunus persica L.*
Varietal Denomination: NJN100

(75) Inventors: Joseph C. Goffreda, Manalapan, NJ (US); Anna M. Voordeckers, East Windsor, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 0 days.

(21) Appl. No.: 11/392,058

(22) Filed: Mar. 29, 2006

(65) Prior Publication Data

US 2007/0234447 P1 Oct. 4, 2007

(51) Int. Cl.
*A01H 5/00* (2006.01)

(52) U.S. Cl. ..... Plt./188

(58) Field of Classification Search ..... Plt./188
See application file for complete search history.

*Primary Examiner*—Anne Marie Grunberg
*Assistant Examiner*—S. B. McCormick-Ewoldt
(74) *Attorney, Agent, or Firm*—Michael J. Medely; Driggs, Hogg & Fry Co., L.P.A.

(57) ABSTRACT

A new and distinct nectarine variety of *Prunus persica* named 'NJN100' is provided. This variety is distinguished from other nectarine varieties by its unique combination of showy flowers, fruit that ripen in early-season, glossy fruit with an attractive red over color and greyed-white ground color, clingstone fruit with a juicy, melting texture and sweet, moderately acidic flavor, and excellent production of firm fruit that maintain their eating quality following cold storage.

6 Drawing Sheets

Latin name of genus and species of the plant claimed: *Prunus persica* L.
Variety denomination: 'NJN100'.

BACKGROUND OF THE INVENTION

The present invention relates to a new and distinct variety of nectarine tree named 'NJN100'. Our new tree resulted from crossing 'B8-9-46-712034' as the seed parent with 'Eastern Glo' nectarine tree, as the pollen parent. The new variety differs from seed parent 'B8-9-46-712034' (unpatented) in that the new variety has large, showy flowers and firm fruit with an attractive, glossy finish, while the seed parent has small, nonshowy flowers and comparatively soft fruit that usually have a poor finish. The new variety differs from pollen parent 'Eastern Glo' (U.S. Plant Pat. No. 7,890) in that the new variety has greyed-white flesh flecked with red, especially towards the skin, while the pollen parent has yellow to golden yellow flesh. The resulting tree was selected when growing in a cultivated area as the $4^{th}$ tree in the $56^{th}$ row of Block K at the Rutgers Fruit Research and Extension Center in Cream Ridge, N.J.

BRIEF SUMMARY OF THE INVENTION

The 'NJN100' variety is distinguished from other nectarine varieties due to the following unique combination of characteristics:

- Round fruit with a low tendency to split for the season.
- Glossy fruit with an attractive red over color and greyed-white ground color.
- Excellent production of firm fruit that ripen in early-season.
- Fruit with a good to excellent eating quality.

The variety was asexually reproduced at the Rutgers Fruit Research and Extension Center in Cream Ridge, N.J. Asexual reproduction of this new variety by budding onto 'Lovell' rootstock (unpatented) shows that the foregoing characteristics are so reproduced.

The following detailed description concerns the original tree, 'NJN100'. The original tree and asexual progeny have been observed growing in a cultivated area in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to The Royal Horticultural Society (R.H.S.) Colour Chart.

BRIEF DESCRIPTION OF THE DRAWINGS

This new variety is illustrated by the accompanying photographic drawings, depicting the peach tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

DETAILED BOTANICAL DESCRIPTION

Figure 1:
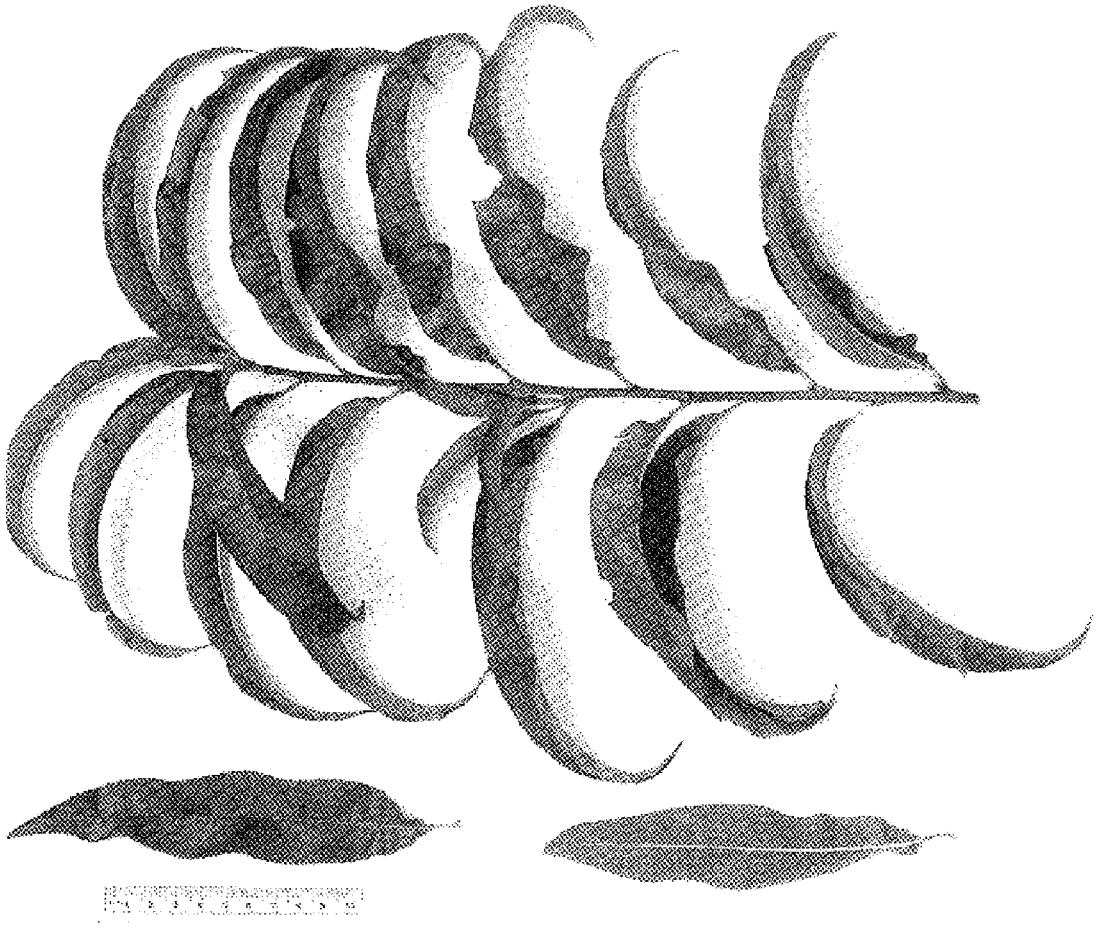
FIG. 1 is a color photograph taken on Aug. 29, 2005 of a characteristic twig of 'NJN100' in late summer bearing typical leaves of the mature foliage.
Figure 2:
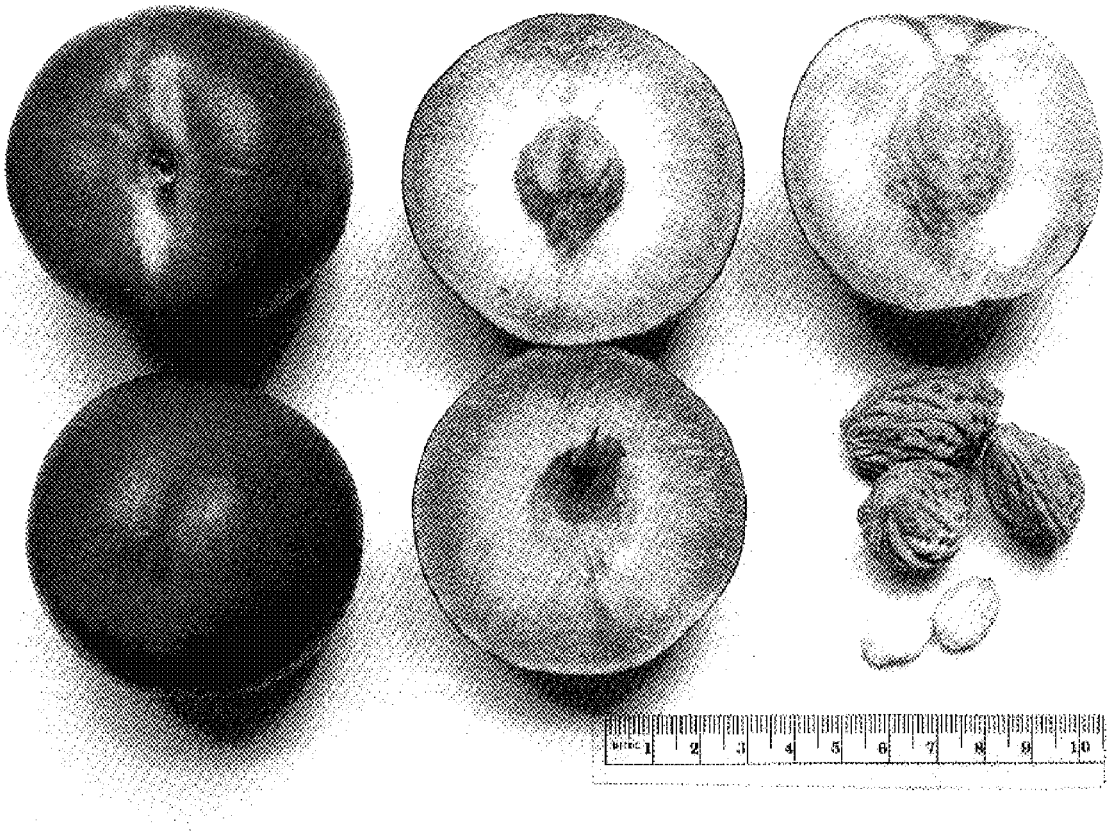
FIG. 2 is a color photograph taken on Aug. 19, 2005 of characteristic mature fruit and stones of 'NJN100'. Whole fruit are presented in two positions and transverse and longitudinal cross sections to show that the pericarp tends to adhere to the pit when the fruit is mature. The stones illustrate the ovoid shape and the pit grooves on the surface of the stone.
Figure 3:
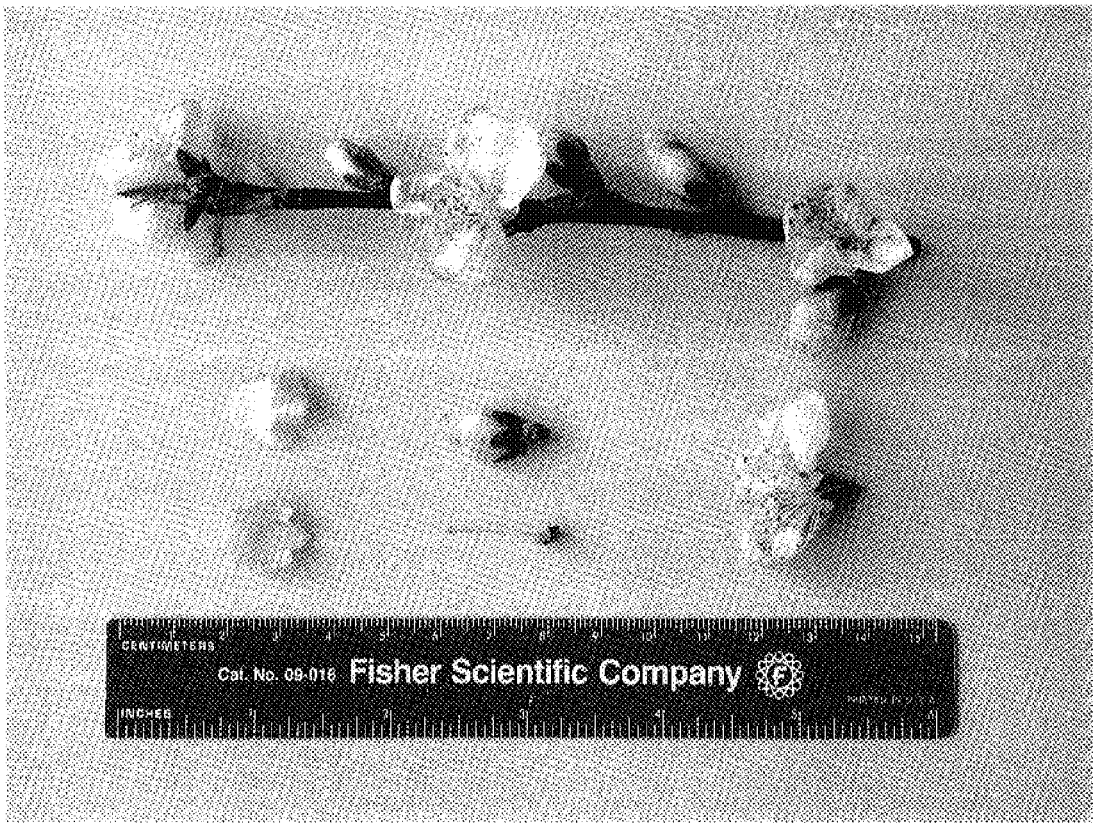
FIG. 3 is a color photograph of a characteristic twig that illustrates the typical flower buds and large, showy flowers of 'NJN100' observed on a tree in Cream Ridge, N.J. on Apr. 16, 2005.
Figure 4:
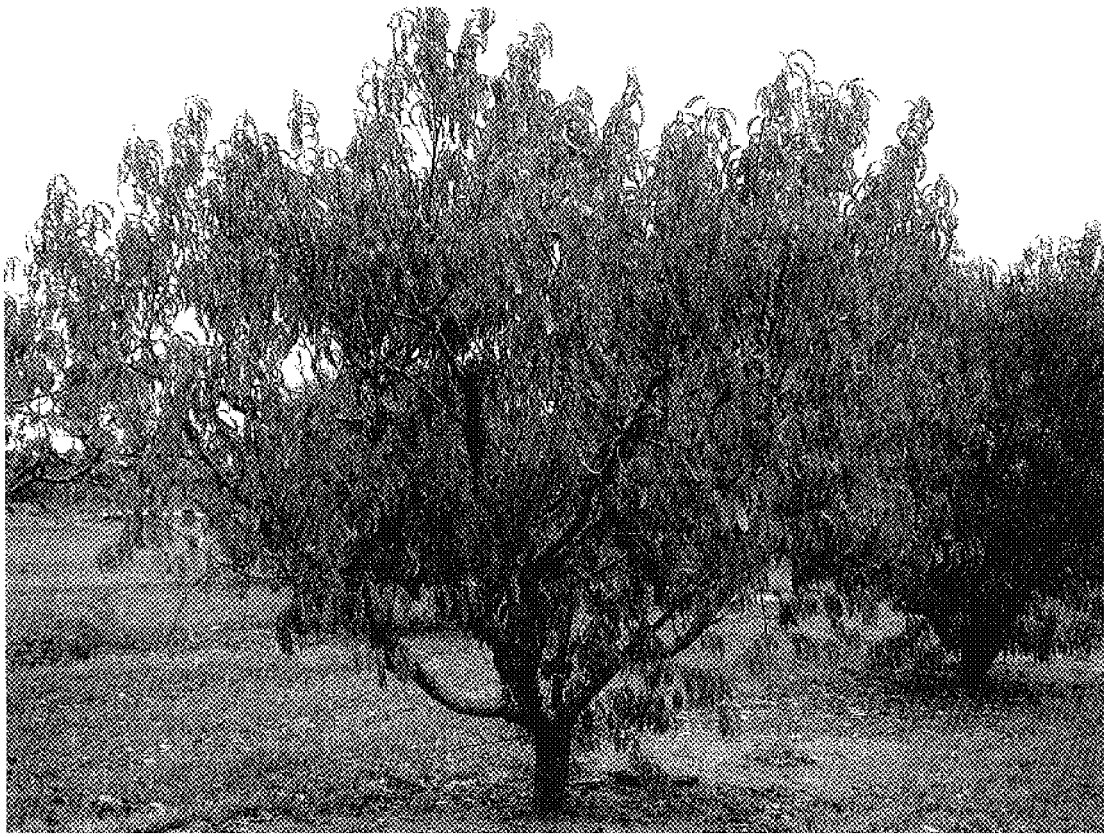
FIG. 4 is a color photograph of a tree of 'NJN100' in early fall that illustrates the spreading growth habit of a tree in Cream Ridge, N.J. on Oct. 27, 2005.
Figure 5:
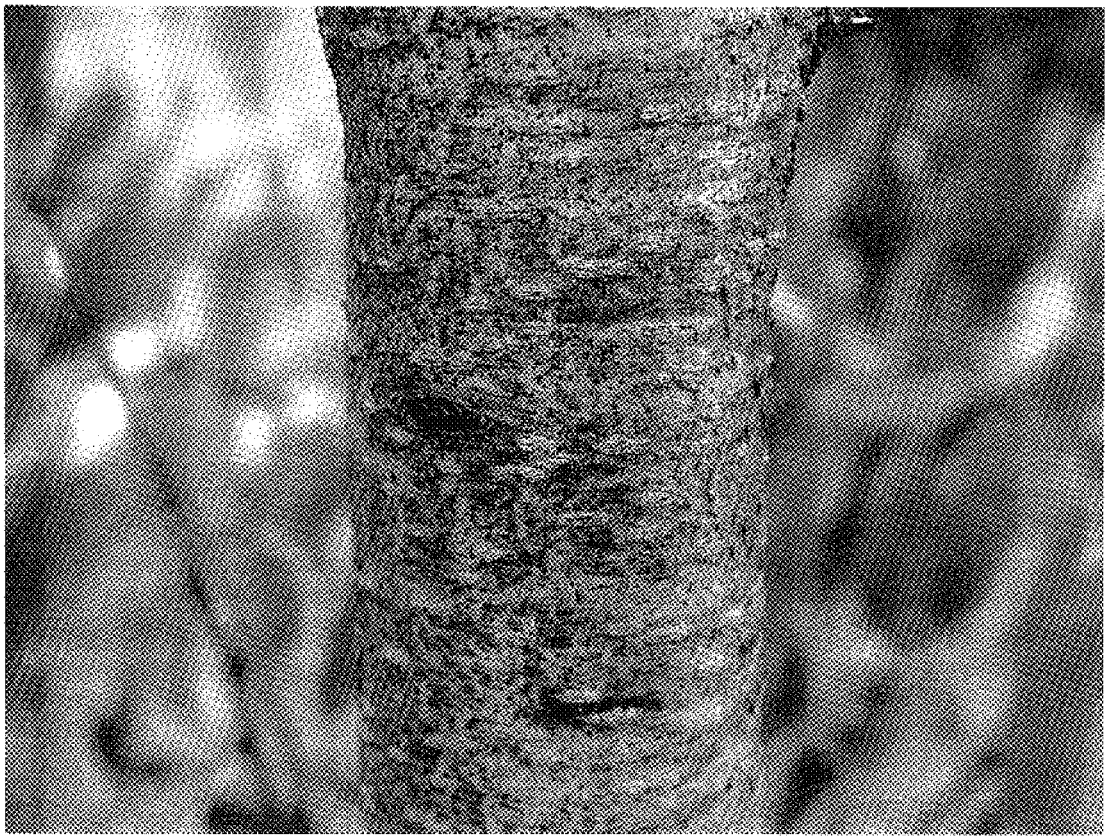
FIG. 5 is a color photograph taken on Oct. 27, 2005 of immature bark of 'NJN100' that illustrates color and the comparatively moderate density of comparatively inconspicuous lenticels on the immature bark.
Figure 6:
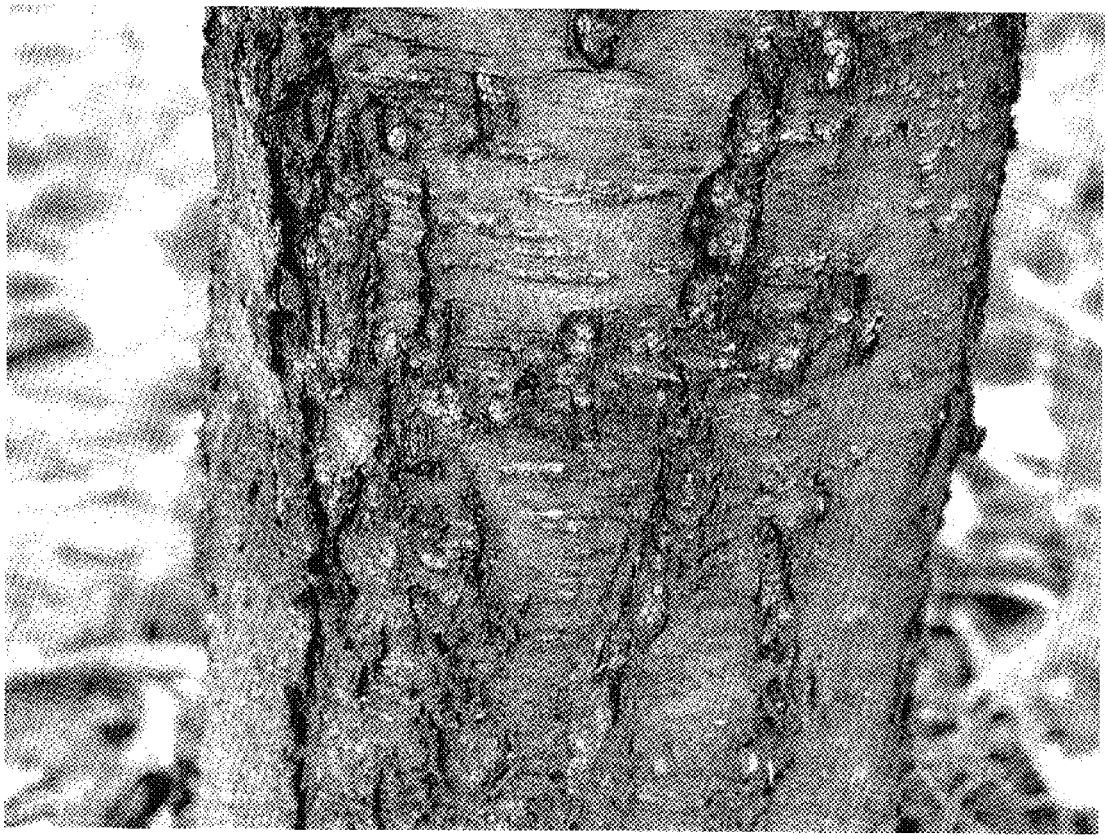
FIG. 6 is a color photograph taken on Oct. 27, 2005 of mature bark of 'NJN100' that illustrates the moderately rough texture of the mature bark.

The following detailed description of the 'NJN100' variety is based on observations of an asexually reproduced tree. The observed tree was nine years of age and growing on 'Lovell' seedling rootstock (unpatented) in Research Block E in Cream Ridge, N.J.

Scientific name: *Prunus persica* L.
Parentage:

| | |
|---|---|
| Seed parent: | B8-9-46-712034. |
| Pollen parent: | 'Eastern Glo'. |

Tree:

| | |
|---|---|
| Vigor: | Vigorous. |
| Plant hardiness zone: | Growth of plants has only been observed in zone 6b. |
| Dormant flower bud cold tolerance: | At least to −16° C. |
| Overall shape: | Spreading. |
| Height: | Slightly above average as compared to other nectarine cultivars. For example, measurement of a typical grafted tree on 'Lovell' seedling rootstock (unpatented) at nine years after planting shows an average height of 4.0 meters when grown in Cream Ridge, New Jersey. |
| Width: | Slightly above average as compared to other nectarine cultivars. For example, measurement of a typical grafted tree on 'Lovell' seedling rootstock (unpatented) at nine years after planting shows an average width of 5.5 meters when grown in Cream Ridge, New Jersey. |
| Caliper: | Nine year old tree is 52 cm in circumference measured at 20 cm from the ground. |

Trunk and branches:

| | |
|---|---|
| Trunk bark texture: | Moderately rough. |
| Trunk bark color: | Greyed-white (RHS 156d). |
| Primary branches: | Branches that are approximately 18 cm in circumference are greyed-orange (RHS 165a) in color, overlaid with greyed-white (RHS 156b). |
| Lenticels: | Moderate density, approximately 2 per square cm; elliptical shape and relatively inconspicuous; typical examples of which measured 5.5 mm in length and 2.5 mm in width; greyed-white (RHS 156d) in color and flecked with greyed-orange (RHS 174b). |
| Branch pubescence: | None. |
| New growth bark: | Color varies between greyed-red (RHS 178a) in sun; color greyed-yellow (RHS 161a) and overlaid with greyed-orange (RHS 176b) in shade. |
| Internodes: | Length averaging 25.8 mm on a one-year shoot. |

Leaves:

| | |
|---|---|
| Texture: | Glabrous. |
| Sheen: | Young leaves semi-glossy with a flat finish on the underside. |
| Length: | About 167 mm to 221 mm, averaging about 197 mm including the petiole. |
| Width: | About 35 mm to 49 mm, averaging about 40 mm. |
| Petiole: | Averaging 12.7 mm long and about 1.5 mm in diameter. |
| Margin: | Serrulate. |
| Margin undulation: | Slight. |
| Form: | Elliptic. |
| Apex: | Acuminate, curved downward. |
| Base: | Cuneate. |
| Venation: | Pinnate. |
| Glands: | |
| Number: | About 2 to 5, averaging about 3.8. |
| Position: | Located on the leaf margin and petiole. |
| Size: | Length averaging 1.1 mm and width averaging 0.9 mm. |
| Form: | Reniform. |
| Stipules: | None observed on mature leaves. |
| Leaf Color: | |
| Upper leaf surface: | Green (between RHS 137b and RHS 137c). |
| Lower leaf surface: | Yellow-green (RHS 147b). |
| Vein: | Yellow-green (RHS 145c). |
| Pubescence: | None. |

Flowers:

| | |
|---|---|
| Size: | Large size, typical flower measuring between 34 mm and 37 mm, averaging about 36 mm across. |
| Color: | |
| Dormant bud: | Grey (RHS 201c) with flecks of brown (RHS 200d). |
| Pink stage bud: | Red-purple (between RHS 62c and RHS 62d). |
| Open flower: | Red (RHS 62d). |
| Petals: | Typically five petals per flower; cupped and round in shape; averaging about 18.0 mm long and 17.0 mm wide. Red (RHS 62d) in color. |
| Petal apex: | Obtuse. |
| Petal base: | Attenuate. |
| Stamens: | |
| Number: | Variable, typical range 37 and 40, averaging 38.2. |
| Length: | Variable, between 12.1 mm and 15.1 mm, averaging 14.0 mm. |
| Filament color: | White (between RHS 155a near the base and RHS 155d towards the apex). |
| Anther color: | Red (RHS 46a). |
| Pistil: | |
| Number: | One. |
| Size: | Length between 19.0 and 20.4 mm, averaging about 19.5 mm. |
| Pistil color: | Yellow-green (RHS 144b). |
| Ovary: | Glabrous and ellipsoid in shape. |

-continued

Sepals:

| | |
|---|---|
| Number: | Five. |
| Pubescence: | Short and low density. |
| Color: | Yellow-green (RHS 148b) with a greyed-red (RHS 178a) over color. |
| Shape: | Triangular, with a rounded apex. |
| Size: | Length averaging 5.0 mm, width averaging 4.3 mm. |
| Nectar cup color: | Greyed-orange (RHS 167c). |
| Pollen: | Abundant; yellow-orange (RHS 20a) in color. |
| Fragrance: | Very slight. |
| Bloom season: | Onset of bloom in 2005 on April 15; full bloom on April 18. |
| Pollination requirements: | Self-pollinating |

Fruit:

| | |
|---|---|
| Size: | Large, averaging about 6.2 cm long, 6.5 cm wide parallel to the suture and 6.5 cm wide perpendicular to the suture. |
| Typical weight: | 142 g. |

Form:

| | |
|---|---|
| Longitudinal section: | Nearly round. |
| Traverse section: | Round. |
| Suture: | Very shallow, extending from the base to apex. |
| Ventral surface: | Typically smooth. |
| Base: | Flat. |
| Apex: | Round. |
| Stem: | Average length of 5.9 mm and an average diameter of 5.5 mm. |

Skin:

| | |
|---|---|
| Thickness: | Average. |
| Surface: | Glabrous, typically glossy. |
| Tenacity: | Average. |
| Astringency: | None. |
| Tendency to crack: | Low. |
| Color: | Mottled red (RHS 53a) over a red (RHS 46b) blush; ground color greyed-white (RHS 156c). |

Fruit Properties:

| | |
|---|---|
| Flesh color: | Greyed-white (between RHS 156c and RHS 156d) flecked with red (RHS 56b), especially towards the skin. |
| Flesh adhesion: | Clingstone. |
| Juice: | Moderate. |
| Texture: | Firm, but melting. |
| Fibers: | Not noticeable. |
| Ripens: | Between July 8 and July 28 at Cream Ridge, New Jersey. |
| Flavor: | Above average, generally sweet and moderately acidic. |
| Soluble solids: | 10.2%. |
| Aroma: | Very slight. |

-continued

| | |
|---|---|
| Eating quality: | Good to excellent. |
| Keeping quality: | Above average. Has held its flavor and firmness for at least 21 days in cold storage at 1° C. to 4° C. |
| Shipping quality: | Very good. Fruit are generally very firm at harvest. No bruising or scaring disorders have been observed. |
| Usage: | Dessert. |
| Market: | Local and long distance. |
| Productivity: | Excellent. Trees have produced a crop in 10 out of 10 years and a full crop in 8 out of 10 years at Cream Ridge, New Jersey. |

Stone:

| | |
|---|---|
| Type: | Clingstone. |
| Form: | Ovoid. |
| Base: | Narrow to medium. |
| Apex: | Wide. |
| Surface: | Pit grooves. |
| Ventral suture: | Medium, may he truncated at the apex. |
| Dorsal ridge: | Low height, narrow width, forming lines of medium depth. |
| External color: | Orange-white (RHS 159a). |
| Internal color when cracked: | Orange-white (RHS 159a). |
| Cavity surface color: | Greyed-orange (RHS 165d). |
| Average stone dry weight: | 4.94 g. |
| Average stone wall thickness: | Varies between 3.6 and 8.1 mm. |
| Size: | Averages about 33.8 mm long, 26.8 mm wide parallel to the dorsal ridge, and 19.6 mm wide perpendicular to the dorsal ridge. |
| Tendency to split: | Low. |

Kernel:

| | |
|---|---|
| Form: | Highly variable; forms only rudimentary seed. |
| Skin color: | Greyed-orange (RHS 165b). |
| Vein color: | Greyed-orange (between RHS 165a and RHS 165b). |
| Viability: | No. |
| Size: | Highly variable; forms only rudimentary seed. |

Plant/fruit disease and pest resistance/susceptibility: No atypical resistances/susceptibilities have been noted under normal cultural practices.

We claim:

1. A new and distinct variety of nectarine tree, substantially as herein shown and described.

* * * * *